United States Patent
Umemoto et al.

(10) Patent No.: US 12,318,227 B2
(45) Date of Patent: Jun. 3, 2025

(54) LEARNED MODEL GENERATION METHOD, TRAINING DATA GENERATION DEVICE, LEARNED MODEL GENERATION DEVICE, AND DISEASE DEVELOPMENT RISK PREDICTION DEVICE

(71) Applicant: NIHON KOHDEN CORPORATION, Tokyo (JP)

(72) Inventors: Takuya Umemoto, Tokorozawa (JP); Jun Motogi, Tokorozawa (JP); Keiichi Sato, Tokorozawa (JP); Wataru Matsuzawa, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 358 days.

(21) Appl. No.: 17/876,032

(22) Filed: Jul. 28, 2022

(65) Prior Publication Data
US 2023/0049898 A1    Feb. 16, 2023

(30) Foreign Application Priority Data

Aug. 10, 2021 (JP) .................................. 2021-130679

(51) Int. Cl.
*A61B 5/02* (2006.01)
*A61B 5/00* (2006.01)

(52) U.S. Cl.
CPC .............. *A61B 5/7275* (2013.01); *A61B 5/02* (2013.01); *A61B 5/7267* (2013.01)

(58) Field of Classification Search
CPC ........ A61B 5/7275; A61B 5/7267; A61B 5/02
(Continued)

(56) References Cited

U.S. PATENT DOCUMENTS

2009/0234202 A1* 9/2009 Goix ...................... A61B 5/415
                                                                 436/86
2017/0031329 A1    2/2017 Inagaki et al.
(Continued)

FOREIGN PATENT DOCUMENTS

JP    2014-54391 A    3/2014
JP    2017-33526 A    2/2017
(Continued)

OTHER PUBLICATIONS

Office Action issued on Dec. 3, 2024 by the Japanese Patent Office in corresponding JP Patent Application No. 2021-130679.

*Primary Examiner* — Nadia A Mahmood
(74) *Attorney, Agent, or Firm* — Sughrue Mion, PLLC

(57) ABSTRACT

A method includes: receiving first data including physiological information obtained from a subject and a first result that a disease is developing; specifying a first time point at which the physiological information included in the first data is obtained; receiving second data including the physiological information obtained from the subject and a second result that the disease is not developing; specifying a second time point at which the physiological information included in the second data is obtained; upon determining that a time interval between the first time point and the second time point is smaller than a first predetermined value, assigning, to the second data, a first training label indicating that the disease is developing and a weighting index that is capable of taking a plurality of values according to the time interval; and performing machine learning of a model by using the second data as training data.

16 Claims, 10 Drawing Sheets

(58) Field of Classification Search
USPC .......................................................... 600/301
See application file for complete search history.

(56) References Cited

U.S. PATENT DOCUMENTS

| | | |
|---|---|---|
| 2019/0265657 A1 | 8/2019 | Inagaki et al. |
| 2022/0146993 A1 | 5/2022 | Inagaki et al. |

FOREIGN PATENT DOCUMENTS

| | | |
|---|---|---|
| JP | 2019-16235 A | 1/2019 |
| JP | 2020-145556 A | 9/2020 |
| WO | 2019/008798 A1 | 1/2019 |

* cited by examiner

LEARNED MODEL GENERATION METHOD, TRAINING DATA GENERATION DEVICE, LEARNED MODEL GENERATION DEVICE, AND DISEASE DEVELOPMENT RISK PREDICTION DEVICE

CROSS-REFERENCE TO RELATED APPLICATIONS

This application is based on and claims priority under 35 USC 119 from Japanese Patent Application No. 2021-130679 filed on Aug. 10, 2021, the contents of which are incorporated herein by reference.

TECHNICAL FIELD

The presently disclosed subject matter relates to a learned model generation method and a learned model generation device that generate a learned model for predicting a disease development risk of a subject based on physiological information obtained from the subject. The presently disclosed subject matter also relates to a training data generation device that generates training data used to generate the learned model. The presently disclosed subject matter also relates to a disease development risk prediction device that predicts a disease development risk of a subject by using the learned model.

BACKGROUND ART

JP-A-2014-054391 discloses a Holter electrocardiograph that obtains an electrocardiogram that is an example of a physiological parameter of a subject. Data corresponding to a measurement waveform of the electrocardiogram is received by an information processing device that is remotely arranged. The information processing device is configured to detect an abnormality in the measurement waveform by analyzing the data and specify the development of a disease such as cardiac insufficiency in the subject.

An object of the presently disclosed subject matter is to predict a disease development risk potentially possessed by a subject.

SUMMARY

A first aspect of the presently disclosed subject matter relates to a learned model generation method for generating a learned model for predicting a disease development risk of a subject based on physiological information obtained from the subject. The learned model generation method includes:
  receiving first data including the physiological information obtained from a first subject and a first result that a disease is developing, the first result being determined based on the physiological information;
  specifying a first time point at which the physiological information included in the first data is obtained;
  receiving second data including the physiological information obtained from the first subject and a second result that the disease is not developing, the second result being determined based on the physiological information;
  specifying a second time point at which the physiological information included in the second data is obtained;
  upon determining that a time interval between the first time point and the second time point is smaller than a first predetermined value, assigning, to the second data, a first training label indicating that the disease is developing and a weighting index that is capable of taking a plurality of values according to the time interval; and
  performing machine learning of a model by using the second data, to which the first training label is assigned, as training data.

A second aspect of the presently disclosed subject matter relates to A training data generation device that generates training data to be used in generating a learned model for predicting a disease development risk of a subject based on physiological information obtained from the subject. The training data generation device includes circuitry configured to:
  receive first data including the physiological information obtained from a first subject and a first result that a disease is developing, the first result being determined based on the physiological information;
  receive second data including the physiological information obtained from the first subject and a second result that the disease is not developing, the second result being determined based on the physiological information;
  specify a first time point at which the physiological information included in the first data is obtained;
  specify a second time point at which the physiological information included in the second data is obtained; and
  upon determining that a time interval between the first time point and the second time point is smaller than a first predetermined value, generate training data by assigning, to the second data, a first training label indicating that the disease is developing and a weighting index that is capable of taking a plurality of values according to the time interval.

A third aspect of the presently disclosed subject matter relates to a learned model generation method for generating a learned model for predicting a disease development risk of a subject based on physiological information obtained from the subject. The learned model generation method includes:
  receiving first data including the physiological information obtained from a first subject and a first result that a disease is developing, the first result being determined based on the physiological information;
  specifying a first time point at which the physiological information included in the first data is obtained;
  receiving second data including the physiological information obtained from the first subject and a second result that the disease is not developing, the second result being determined based on the physiological information;
  specifying a second time point at which the physiological information included in the second data is obtained;
  assigning, to the second data, a first training label indicating that the disease is developing, upon determining that a time interval between the first time point and the second time point is smaller than a first predetermined value;
  assigning, to the second data, a second training label indicating that the disease is not developing, upon determining that the second time point is earlier than a reference time point by a second predetermined value or more; and
  performing machine learning of a model by using, as training data, at least one of the second data to which the first training label is assigned and the second data to which the second training label is assigned.

A fourth aspect of the presently disclosed subject matter relates to a training data generation device that generates training data to be used in generating a learned model for predicting a disease development risk of a subject based on physiological information obtained from the subject. The device includes circuitry configured to:

receive first data including the physiological information obtained from a first subject and a first result that a disease is developing, the first result being determined based on the physiological information;

receive second data including the physiological information obtained from the first subject and a second result that the disease is not developing, the second result being determined based on the physiological information; and specify a first time point at which the physiological information included in the first data is obtained;

specify a second time point at which the physiological information included in the second data is obtained; and generate training data by assigning a first training label indicating that the disease is developing to the second data upon determining that a time interval between the first time point and the second time point is less than a first predetermined value, and by assigning a second training label indicating that the disease is not developing to the second data upon determining that the second time point is earlier than a reference time point by a second predetermined value or more.

A fifth aspect of the presently disclosed subject matter relates to a learned model generation device that generates a learned model for predicting a disease development risk of a subject based on physiological information obtained from the subject. The device includes circuitry configured to: receive training data generated by the training data generation device according to the second or fourth aspect; and perform machine learning of a model by using the training data.

A sixth aspect of the presently disclosed subject matter relates to a disease development risk prediction device including circuitry configured to: receive physiological information obtained from a subject; input the physiological information to the learned model generated by the learned model generation device according to the fifth aspect; predict a disease development risk of the subject based on a prediction result output from the learned model; and output information corresponding to the disease development risk.

DESCRIPTION OF EMBODIMENTS

Examples of an embodiment will be described in detail below with reference to the accompanying drawings.

The expression "at least one of A and B" used in the present specification for two main bodies A and B includes a case where only A is specified, a case where only B is specified, and a case where both A and B are specified. Each of the main bodies A and B may be singular or plural unless otherwise specified.

The expression "at least one of A, B, and C" used in the present specification for three main bodies A, B, and C includes a case where only A is specified, a case where only B is specified, a case where only C is specified, a case where A and B are specified, a case where B and C are specified, a case where A and C are specified, and a case where all of A, B, and C are specified. Each of the main bodies A, B, and C may be singular or plural unless otherwise specified. The same applies to a case where four or more bodies are described.

Figure 1:
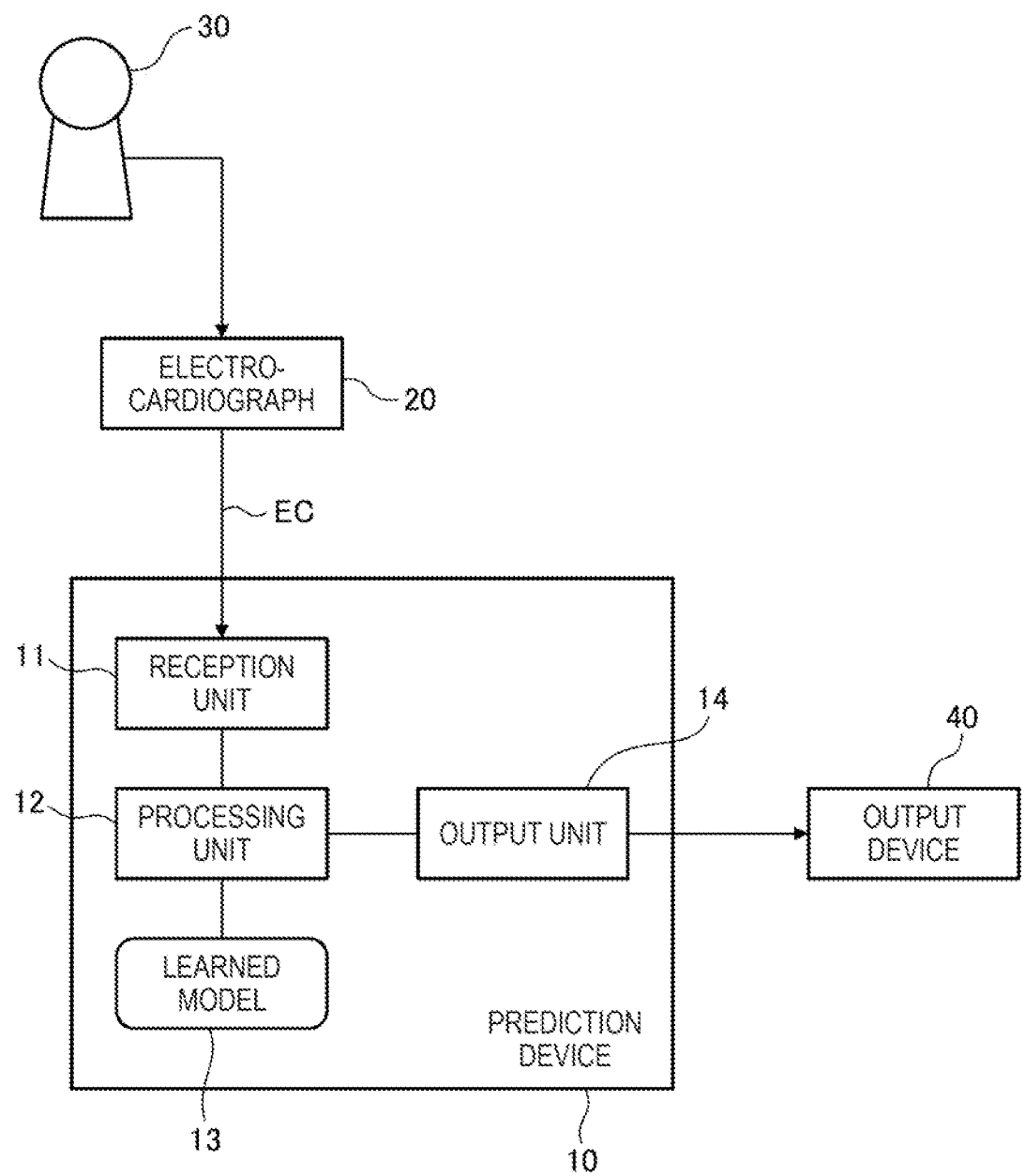
FIG. 1 illustrates a functional configuration of a prediction device according to an embodiment.

FIG. 1 illustrates a configuration of a prediction device 10 according to an embodiment. The prediction device 10 is configured to predict a risk of atrial fibrillation occurring in a subject 30 based on an electrocardiogram waveform obtained from the subject 30 through an electrocardiograph 20. The electrocardiogram waveform is an example of a physiological signal waveform, and is an example of physiological information. The atrial fibrillation is an example of a cardiac disease. The risk of occurrence of the atrial fibrillation is an example of a disease development risk.

The prediction device 10 can include a reception unit 11. The reception unit 11 is configured as an interface through which electrocardiogram data EC corresponding to the electrocardiogram waveform of the subject 30 obtained by the electrocardiograph 20 is received. The electrocardiogram data EC corresponds to change over time of a bioelectric potential obtained within predetermined measurement time in electrodes attached to a body surface of the subject 30.

The prediction device 10 can include a processing unit 12. The processing unit 12 is configured to perform processing of obtaining probability of occurrence of atrial fibrillation in the subject 30 by inputting the electrocardiogram data EC received by the reception unit 11 to a learned model 13. The learned model 13 according to the present example is a prediction algorithm generated through machine learning using a neural network to be described later. The learned model 13 is configured to receive, as an input, the electrocardiogram data EC corresponding to the electrocardiogram of the subject 30, and output the probability of occurrence of atrial fibrillation in the subject 30 as a prediction result. The prediction result may be associated with a score (for example, any of values from 1 to 5) or the like corresponding to the predicted probability.

The prediction device 10 can include an output unit 14. The processing unit 12 is configured to output, from the output unit 14, prediction data PR corresponding to the probability predicted by the learned model 13. That is, the output unit 14 is configured as an interface capable of outputting the prediction data PR.

The prediction data PR is transmitted to an output device 40. The output device 40 is configured to notify, based on the prediction data PR, a user of the risk of occurrence of atrial fibrillation in the subject 30 predicted by the prediction device 10. The notification is performed using at least one of a visual notification, an auditory notification, and a tactile notification.

Figure 2:
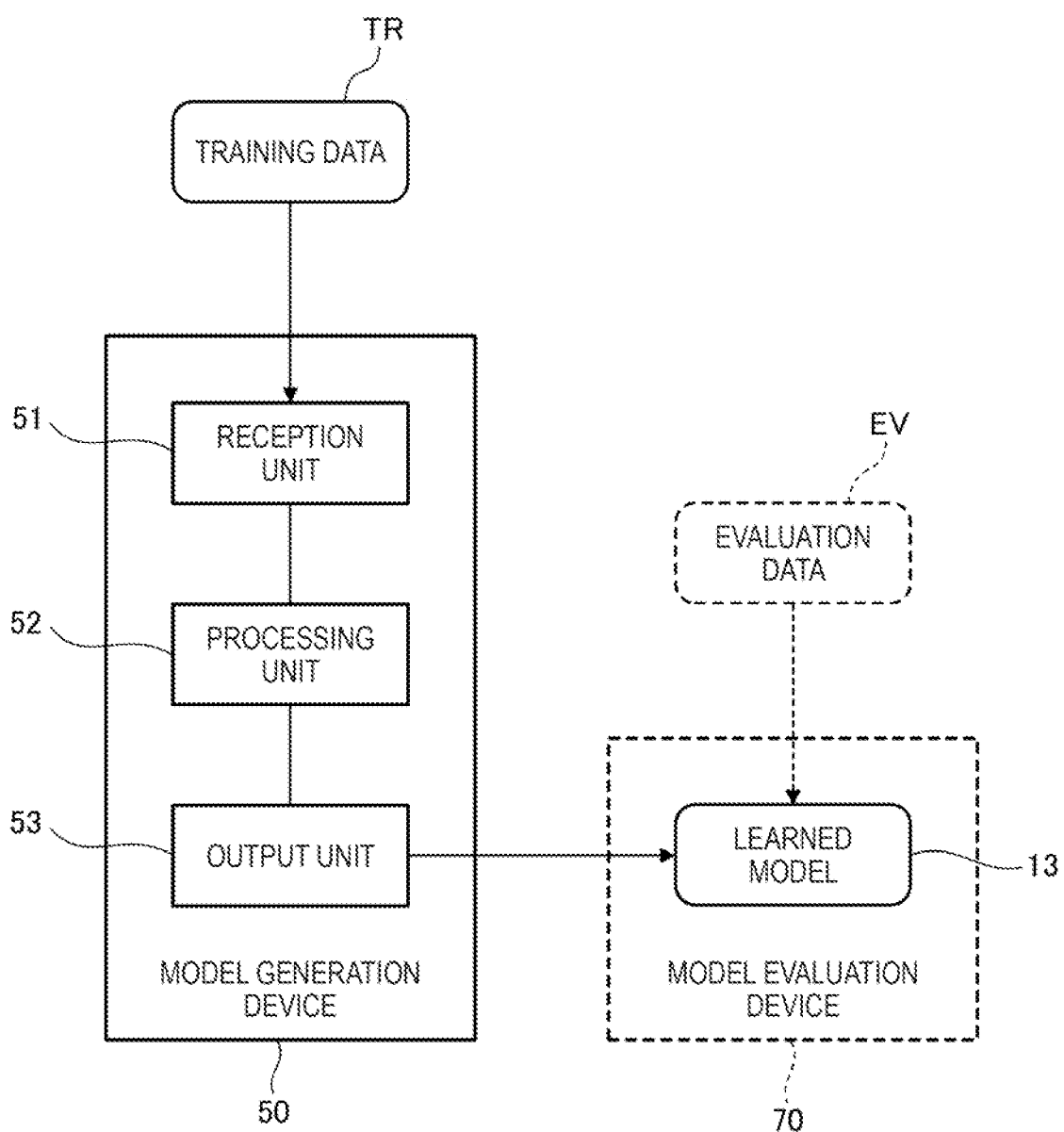
FIG. 2 illustrates a functional configuration of a model generation device according to an embodiment.

The learned model 13 is generated by a model generation device 50 illustrated in FIG. 2. That is, the model generation device 50 is configured to generate the learned model 13 to be installed in the prediction device 10.

The model generation device 50 can include a reception unit 51. The reception unit 51 is configured as an interface through which training data TR is received. The training data TR includes an electrocardiogram waveform obtained from a certain subject and a training label indicating whether the subject is suffering from atrial fibrillation. That is, the training data TR is for teaching by what kind of electrocardiogram waveform obtained from a subject the subject can be determined to be suffering from atrial fibrillation (or not to be suffering from atrial fibrillation).

The model generation device 50 can include a processing unit 52. The processing unit 52 is configured to generate the learned model 13 by causing a neural network to perform learning using the training data TR. As processing of causing the neural network to perform learning, a known method related to supervised learning is appropriately used.

The model generation device 50 can include an output unit 53. The output unit 53 is configured as an interface through which the learned model 13 generated by the processing unit 52 is output in a form that can be installed in the prediction device 10.

Figure 3:
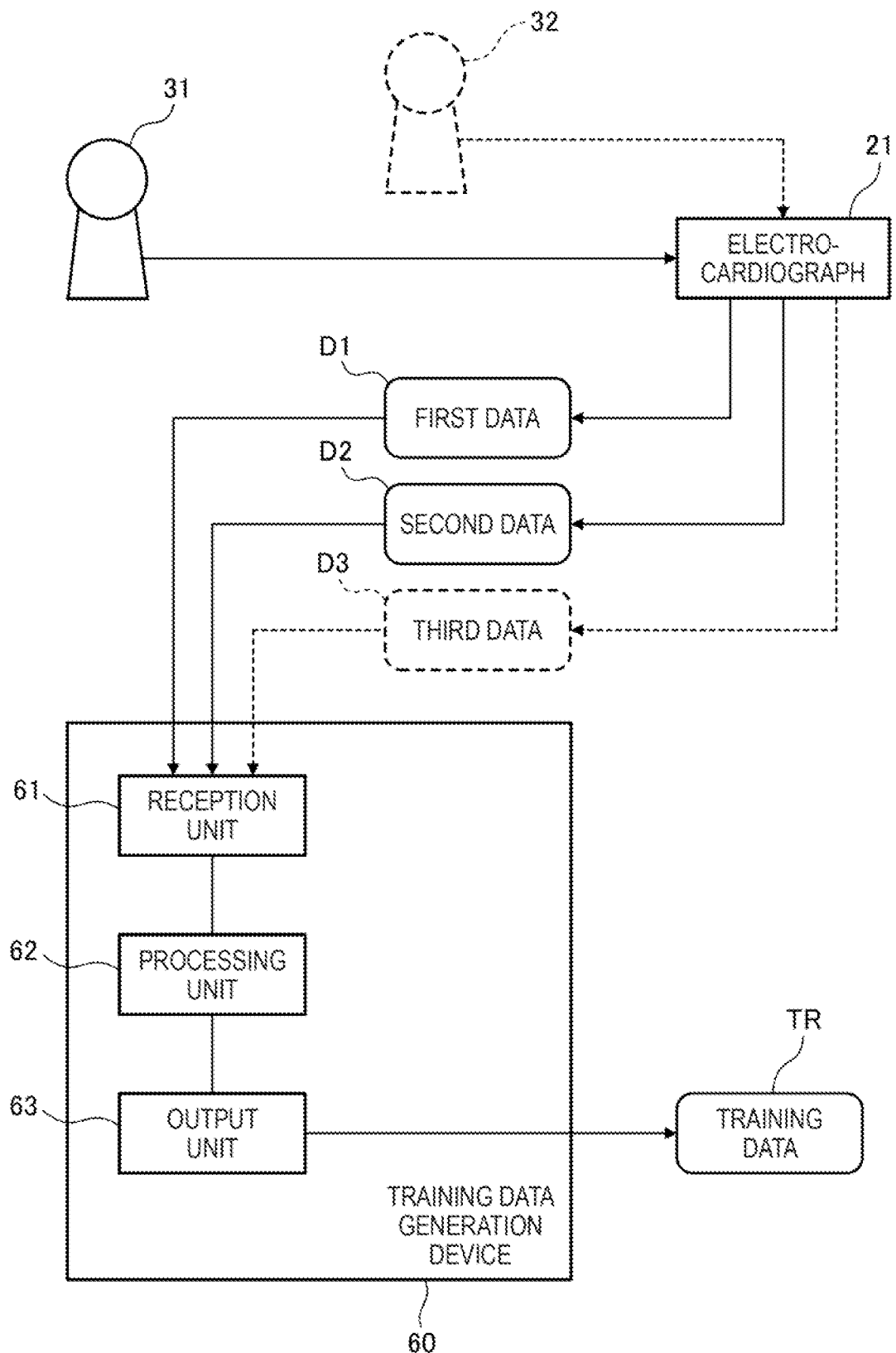
FIG. 3 illustrates a functional configuration of a training data generation device according to an embodiment.

The training data TR is generated by a training data generation device 60 illustrated in FIG. 3. That is, the training data generation device 60 is configured to generate the training data TR used for machine learning executed by the model generation device 50.

The training data generation device 60 can include a reception unit 61. The reception unit 61 is configured as an interface capable of receiving first data D1 and second data D2. The first data D1 and the second data D2 are generated based on an electrocardiogram waveform that is obtained from a subject 31 by an electrocardiograph 21. The subject 31 is an example of a first subject. The electrocardiograph 21 may be the same device as the electrocardiograph 20 illustrated in FIG. 1, or may be a different device. The electrocardiogram waveform may be obtained through a medical information database or the like.

Figure 4:
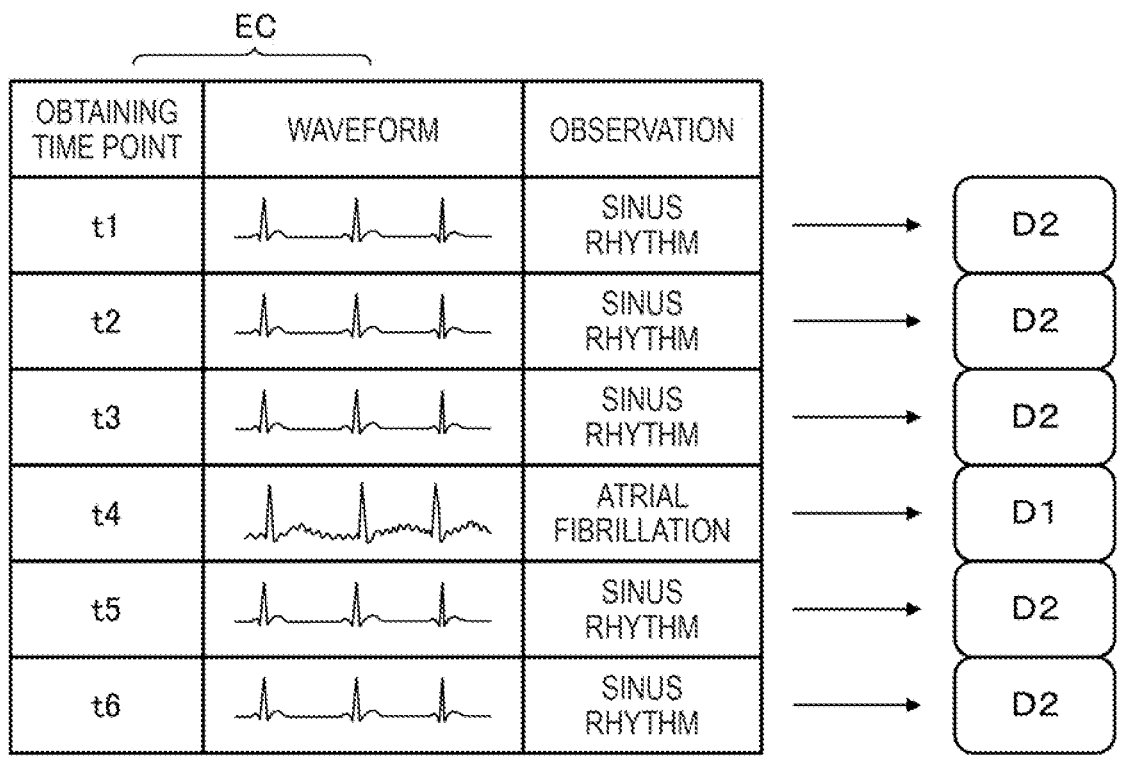
FIG. 4 illustrates a configuration of first data and second data in FIG. 3.

As illustrated in FIG. 4, each of the first data D1 and the second data D2 includes, as information, an obtained electrocardiogram waveform, a time point at which the electrocardiogram waveform is obtained, and an observation as to whether atrial fibrillation has occurred, which is assigned to the electrocardiogram waveform. More specifically, the first data D1 includes a determination result that atrial fibrillation has occurred. The second data D2 includes a determination result that atrial fibrillation has not occurred. The observation may be assigned through visual confirmation by a medical worker, or may be assigned by an algorithm for automatically determining atrial fibrillation that can be installed in the electrocardiograph 21 or the like.

As illustrated in FIG. 3, the training data generation device 60 can include a processing unit 62. The processor 62 is configured to specify a time point at which an electrocardiogram waveform included in the first data D1 is obtained as a first time point, specify a time point at which an electrocardiogram waveform included in the second data D2 is obtained as a second time point, and when a time interval between the first time point and the second time point is smaller than a first predetermined value T1, generate the training data TR by assigning, to the second data D2, both a weighting index that can take a plurality of values according to the time interval and a first training label indicating that atrial fibrillation has occurred.

The training data generation device 60 can include an output unit 63. The processing unit 62 is configured to output the generated training data TR from the output unit 63. That is, the output unit 63 is configured as an interface capable of outputting the training data TR.

Figure 5:
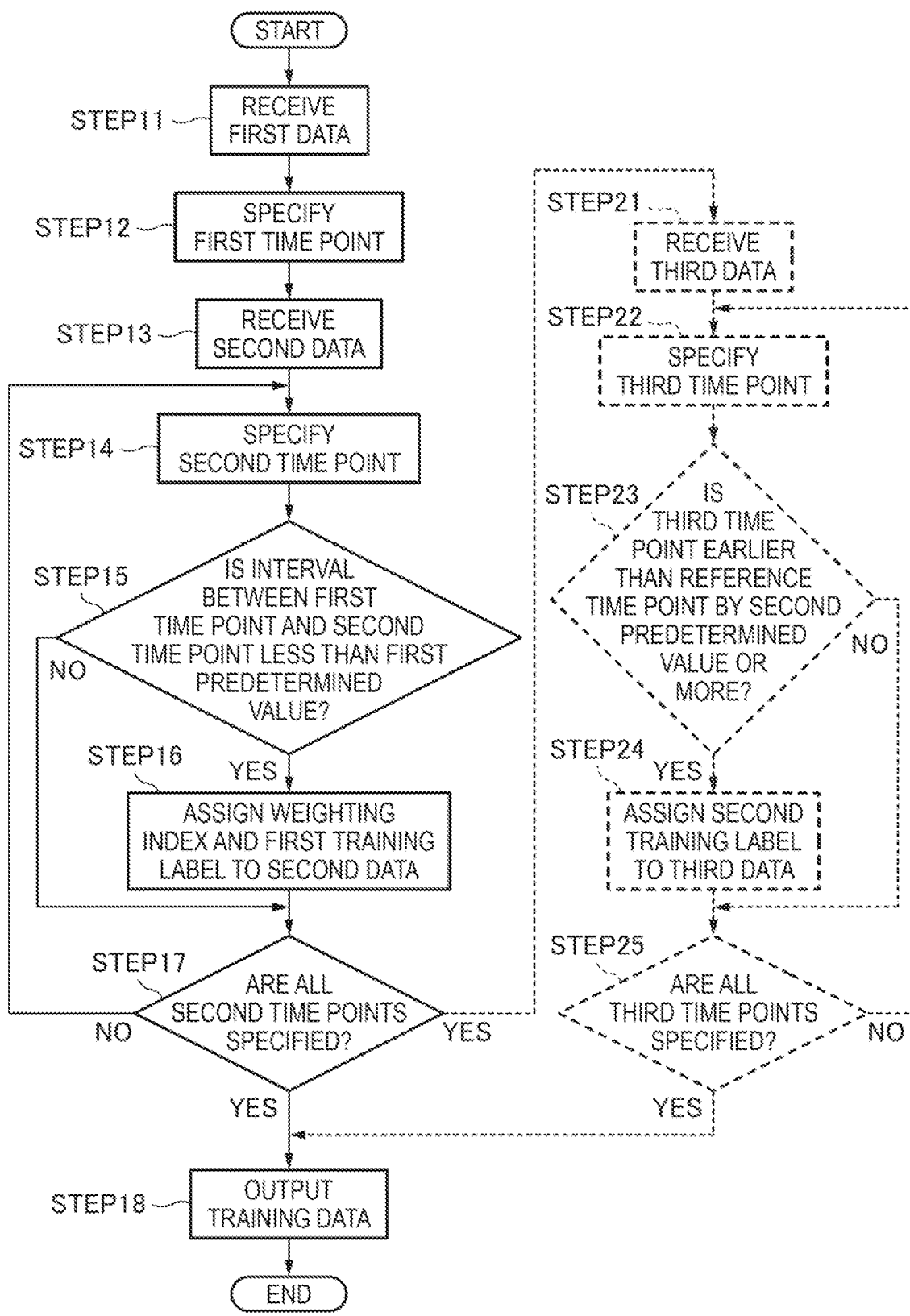
FIG. 5 illustrates an example of a flow of processing executed by a processing unit of FIG. 3.

FIG. 5 illustrates an example of a flow of processing performed by the processing unit 62. A case where the processing is performed on the first data D1 and the second data D2 illustrated in FIG. 4 will be described with reference to FIG. 6.

The processing unit 62 obtains the first data D1 through the reception unit 61 (STEP 11). That is, the processing unit 62 obtains data including an electrocardiogram waveform in which it is determined that atrial fibrillation has occurred.

Subsequently, the processing unit 62 specifies, as a first time point, a time point at which the electrocardiogram waveform included in the first data D1 is obtained (STEP 12). In the example illustrated in FIG. 6, a time point t4 is specified as the first time point.

Subsequently, the processing unit 62 obtains the second data D2 through the reception unit 61 (STEP 13 in FIG. 5). That is, the processing unit 62 obtains data including an electrocardiogram waveform in which it is determined that atrial fibrillation has not occurred.

Subsequently, the processing unit 62 specifies, as a second time point, a time point at which the electrocardiogram waveform included in the second data D2 is obtained (STEP 14).

Subsequently, the processing unit 62 determines whether a time interval between the specified second time point and the specified first time point is smaller than the first predetermined value T1 (STEP 15). An example of the first predetermined value T1 is 30 days.

When the time interval is smaller than the first predetermined value T1 (YES in STEP 15), the processing unit 62 assigns a first training label indicating that atrial fibrillation has occurred, to the second data D2 subjected to the specification of the second time point in STEP 14 (STEP 16).

At this time, the processing unit 62 assigns a weighting index to the second data D2 together with the first training label. The weighting index represents a degree to which teaching of the first training label (that is, atrial fibrillation has occurred) is considered when machine learning based on the training data TR is performed.

Figure 7:
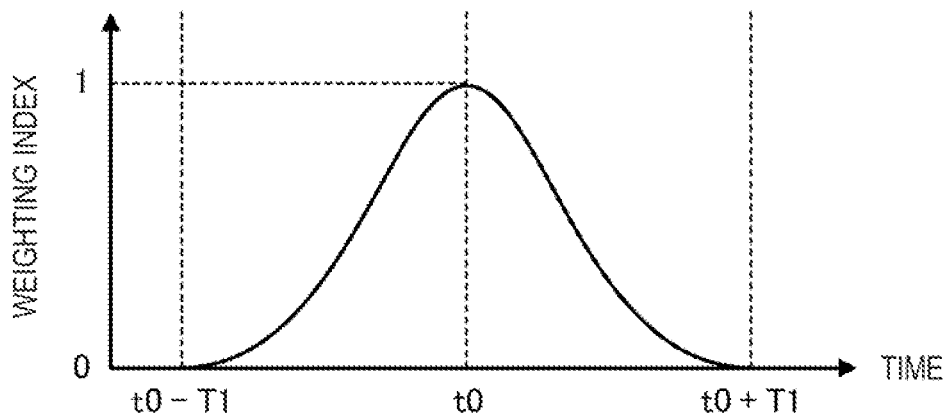
FIG. 7 illustrates an example of a weighting index used in the processing of FIG. 5.

As illustrated in FIG. 7, the weighting index is set to take a plurality of values in accordance with a time interval from a reference time point t0 at which the electrocardiogram waveform included in the first data D1 is obtained. In the example of FIG. 7, the value of the weighting index is 1 at the reference time point W. As the time interval from the reference time point t0 increases, the value of the weighting index decreases, presenting normal distribution of the values of the weighing index. When the time interval from the reference time point t0 reaches the first predetermined value T1, the value of the weighting index is 0. The decrease in normal distribution is an example of a nonlinear decrease.

Figure 8:
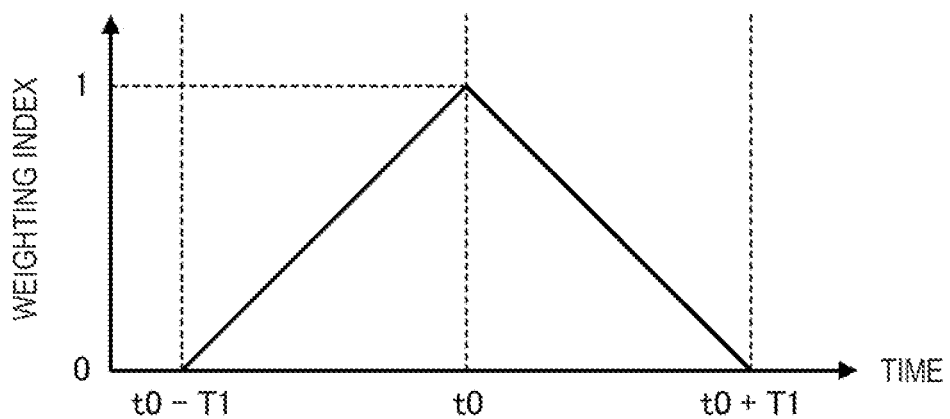
FIG. 8 illustrates another example of the weighting index used in the processing of FIG. 5.
Figure 9:
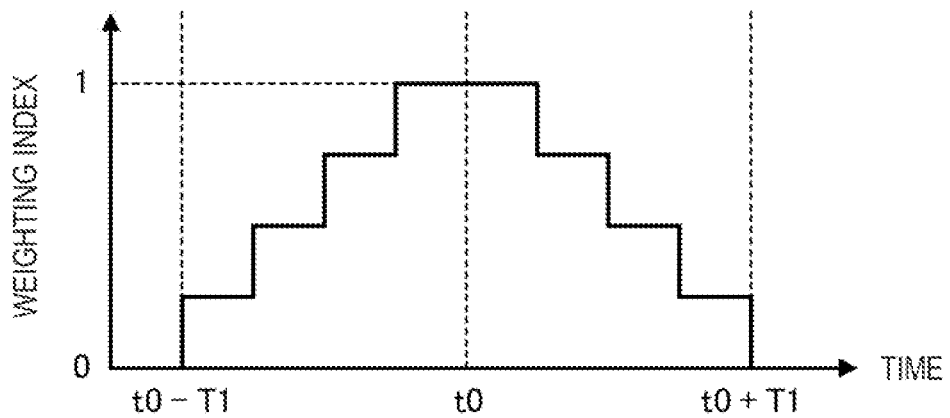
FIG. 9 illustrates another example of the weighting index used in the processing of FIG. 5.

As long as the weighting index can take a plurality of values within a range in which the time interval from the reference time point to is smaller than the first predetermined value T1, the way of change of the weighting index can be determined as appropriate. For example, as illustrated in FIG. 8, the value of the weighting index may linearly decrease as the time interval from the reference time point t0 increases. Alternatively, as illustrated in FIG. 9, the value of the weighting index may decrease stepwise as the time interval from the reference time point t0 increases.

Subsequently, the processing unit 62 determines whether the second time point is specified for all pieces of the second data. D2 (STEP 17 in FIG. 5). When it is determined that the second time point is not specified for all pieces of the second data D2 (NO in STEP 17), the processing is returned to STEP 14, and the second time point is specified for another piece of second data D2.

When it is determined that the time interval between the specified second time point and the specified first time point is not smaller than the first predetermined value T1 (NO in STEP 15), the processing proceeds to STEP 17.

Figure 6:
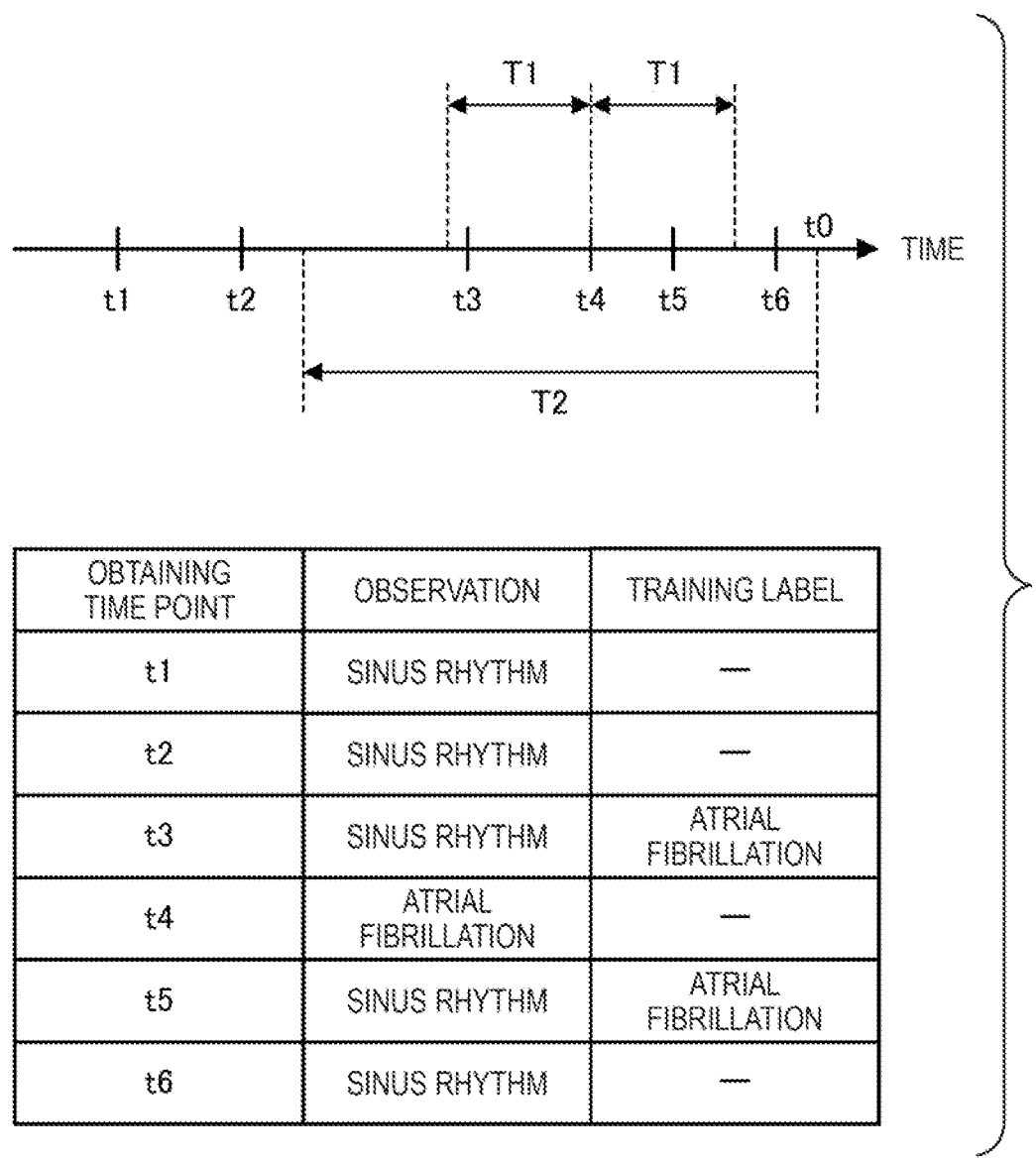
FIG. 6 is a diagram for illustrating processing executed by the processing unit of FIG. 3.

In the example illustrated in FIG. 6, time points t1, t2, t3, t5, and to are specified as the second time points. Since a time interval between the time point t3 among the time points and the time point 14 is smaller than the first predetermined value T1, the processing unit 62 assigns a first training label indicating that atrial fibrillation has occurred, to the second data D2 that is based on an electrocardiogram waveform obtained at the time point t3. The same processing is also performed on the second data D2 that is based on an electrocardiogram waveform obtained at the time point t5.

The time interval from the time point t4, at which the electrocardiogram waveform included in the first data D1 is obtained, to the time point t3 is longer than a time interval from the time point t4 to the time point t5. Therefore, when the weighting index illustrated in FIG. 7 or 8 is used, a value of the weighting index assigned to the second data D2 that is based on the electrocardiogram waveform obtained at the time point t3 is smaller than a value of the weighting index assigned to the second data D2 that is based on the electrocardiogram waveform obtained at the time point t5. When the weighting index illustrated in FIG. 9 is used, the value of the weighting index does not always decrease even if the time interval from the time point t4 increases.

In the example illustrated in FIG. 6, since a time interval from each of the time points t1, t2, and t6 to the time point t4 is not smaller than the first predetermined value T1, the processor 62 does not assign the first training label to the second data D2 that is based on an electrocardiogram waveform obtained at each time point.

Subsequently, the processing unit 62 outputs the second data D2, to which the first training label is assigned together with the weighting index, from the output unit 63 as the training data TR (STEP 18 of FIG. 5).

The training data TR generated as described above is used for machine learning of the neural network that is executed by the model generation device 50, as described with reference to FIG. 2. The learned model 13 generated through the machine learning is installed in the prediction device 10 illustrated in FIG. 1.

Even for an electrocardiogram waveform to which an observation of sinus rhythm is assigned, if a time interval between a time point, at which the electrocardiogram waveform is obtained, and a time point, at which an electrocardiogram waveform in which it is determined that atrial fibrillation has occurred is obtained, is not so long, there is a possibility that some factor that is a sign of atrial fibrillation or some factor affected by atrial fibrillation is included in the electrocardiogram waveform of sinus rhythm. According to the above configuration, it is possible to generate training data, to which a training label indicating that atrial fibrillation has occurred is assigned, for an electrocardiogram waveform of sinus rhythm satisfying such a temporal condition.

Therefore, a learned model generated through machine learning using such training data can output a prediction result that there is a risk of occurrence of atrial fibrillation, with respect to an input of an electrocardiogram waveform in which sinus rhythm is determined. Accordingly, it is possible to predict a risk of occurrence of atrial fibrillation potentially possessed by a subject.

In addition, the first training label indicating that atrial fibrillation has occurred is assigned a weighting index that can take a plurality of values according to the time interval. Accordingly, it is possible to generate training data having a different probability of the risk of occurrence of atrial fibrillation that is predicted based on an electrocardiogram waveform indicating sinus rhythm. Therefore, it is possible to perform more precise machine learning, and thus it is possible to more precisely predict the risk of occurrence of atrial fibrillation.

As illustrated in FIG. 3, the reception unit 61 of the training data generation device 60 may be configured as an interface through which third data D3 can be obtained. The third data D3 is generated based on an electrocardiogram waveform obtained from a subject 32 by the electrocardiograph 21. The subject 32 is different from the subject 31. For example, the subject 31 may be a patient having a medical history of atrial fibrillation, whereas the subject 32 may be a patient not having a medical history of atrial fibrillation. The subject 32 is an example of a second subject. The electrocardiograph for obtaining the electrocardiogram waveform of the subject 32 does not necessarily need to be the same device as the electrocardiograph 21.

The third data D3 has the same configuration as the second data D2 illustrated in FIG. 4. That is, the third data D3 includes an electrocardiogram waveform obtained by the electrocardiograph 21, a time point at which the electrocardiogram waveform is obtained, and a determination result given by a medical worker for the electrocardiogram waveform that atrial fibrillation has not occurred.

In this case, the processing unit 62 of the training data generation device 60 specifies, as a third time point, a time point at which an electrocardiogram waveform included in the third data D3 is obtained, and when the third time point is earlier than the reference time point by a second predetermined value T2 or more, and generates the training data TR by assigning, to the third data D3, a second training, label indicating that atrial fibrillation has not occurred.

A flow of processing executed by the processing unit 62 on the third data D3 illustrated in FIG. 10 will be described with reference to FIG. 5.

When it is determined that the second time point is specified for all pieces of the second data D2 (YES in STEP 17 of FIG. 5), the processing unit 62 obtains the third data D3 through the reception unit 61 (STEP 21).

Subsequently, the processing unit 62 specifies, as a third time point, a time point at which the electrocardiogram waveform included in the third data D3 is obtained (STEP 22).

Subsequently, the processing unit 62 determines whether the specified third time point is earlier than the reference time point 10 by the second predetermined value T2 or more (STEP 23). Examples of the reference time point t0 include a time point at which the present processing is performed, a time point at which the latest electrocardiogram waveform is obtained from the subject 32, and the like. An example of the second predetermined value T2 is one year.

When it is determined that the specified third time point is earlier than the reference time point t0 by the second predetermined value T2 or more (YES in STEP 23), the processing unit 62 assigns, to the third data D3 obtained in STEP 21, a second training label indicating that atrial fibrillation has not occurred (STEP 24).

Subsequently, the processing unit 62 determines whether the third time point is specified for all pieces of the third data D3 (STEP 25). When it is determined that the third time point is not specified for all pieces of the third data D3 (NO in STEP 25), the processing is returned to STEP 22, and the third time point is specified for another piece of third data D3.

When it is determined that the specified third time point is not earlier than the reference time point to by the second predetermined value T2 or more (NO in STEP 23), the processing proceeds to STEP 25.

Figure 10:
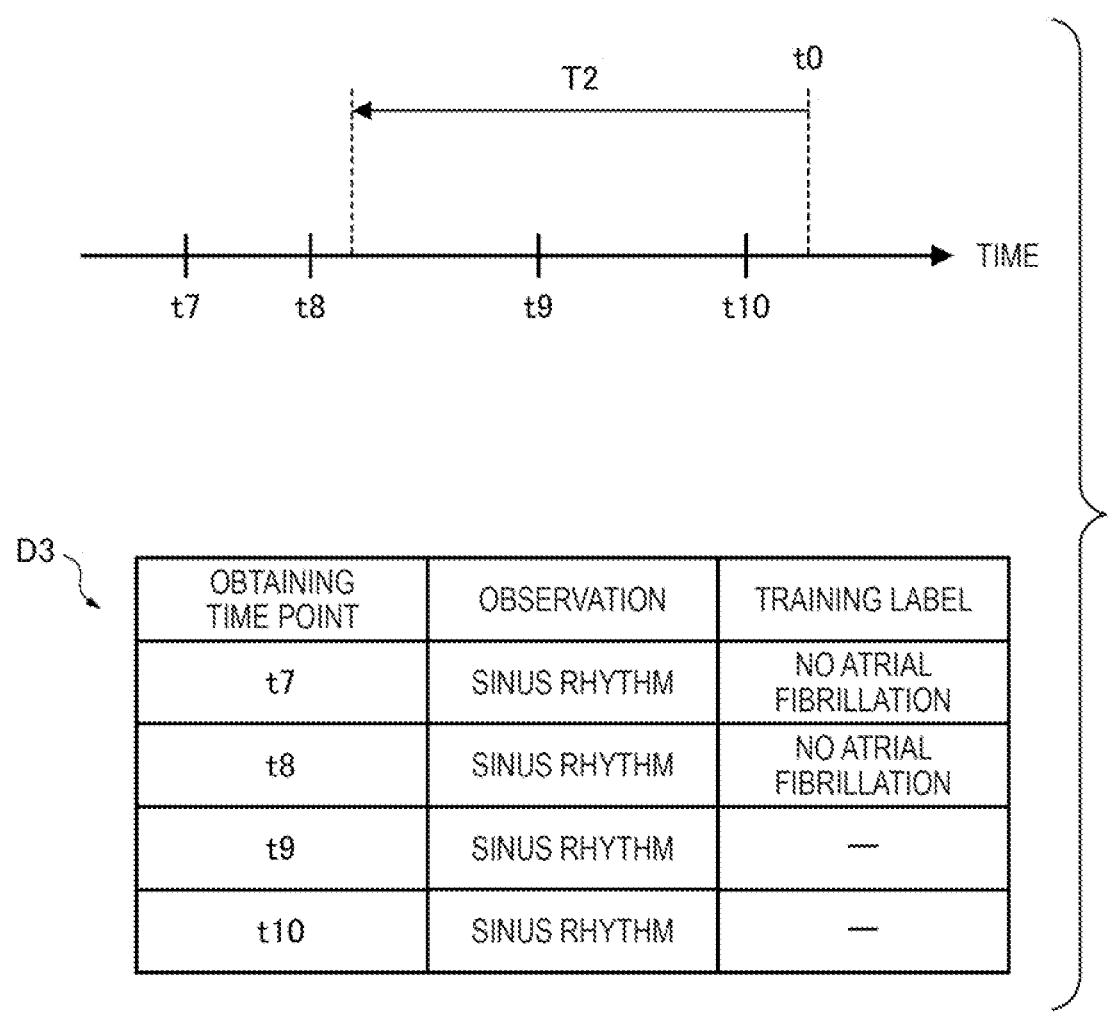
FIG. 10 is a diagram for illustrating processing executed by the processing unit of FIG. 3.

In the example illustrated in FIG. 10, time points t7, t8, t9, and t10 are specified as the third time points. Since the time point t7 and the time point t8 among these time points are earlier than the reference time point t0 by the second predetermined value T2 or more, the processing unit 62 assigns a second training label indicating that atrial fibrillation has not occurred, to the third data D3 that is based on electrocardiogram waveforms obtained at the time point t7 and the time point t8, respectively.

Thereafter, the processing unit 62 outputs, from the output unit 63, the training data TR that includes both the second data D2, to which the first training label and the weighting index are assigned, and the third data D3 to which the second training label is assigned (STEP 18 of FIG. 5).

There is a high probability that an electrocardiogram waveform, which shows sinus rhythm and is obtained sufficiently before the reference time point to, does not include a factor involved in atrial fibrillation. In other words, the second predetermined value T2 is preferably set to such a length that, even when atrial fibrillation occurred in a subject, influence thereof can be ignored. According to the above processing, the second training label indicating that atrial fibrillation has not occurred is positively assigned to such an electrocardiogram waveform and included in the training data TR, and thus it is possible to enhance the effect of machine learning for classifying, based on presence or absence of the risk of occurrence of atrial fibrillation, electrocardiogram waveforms indicating sinus rhythm.

Figure 11:
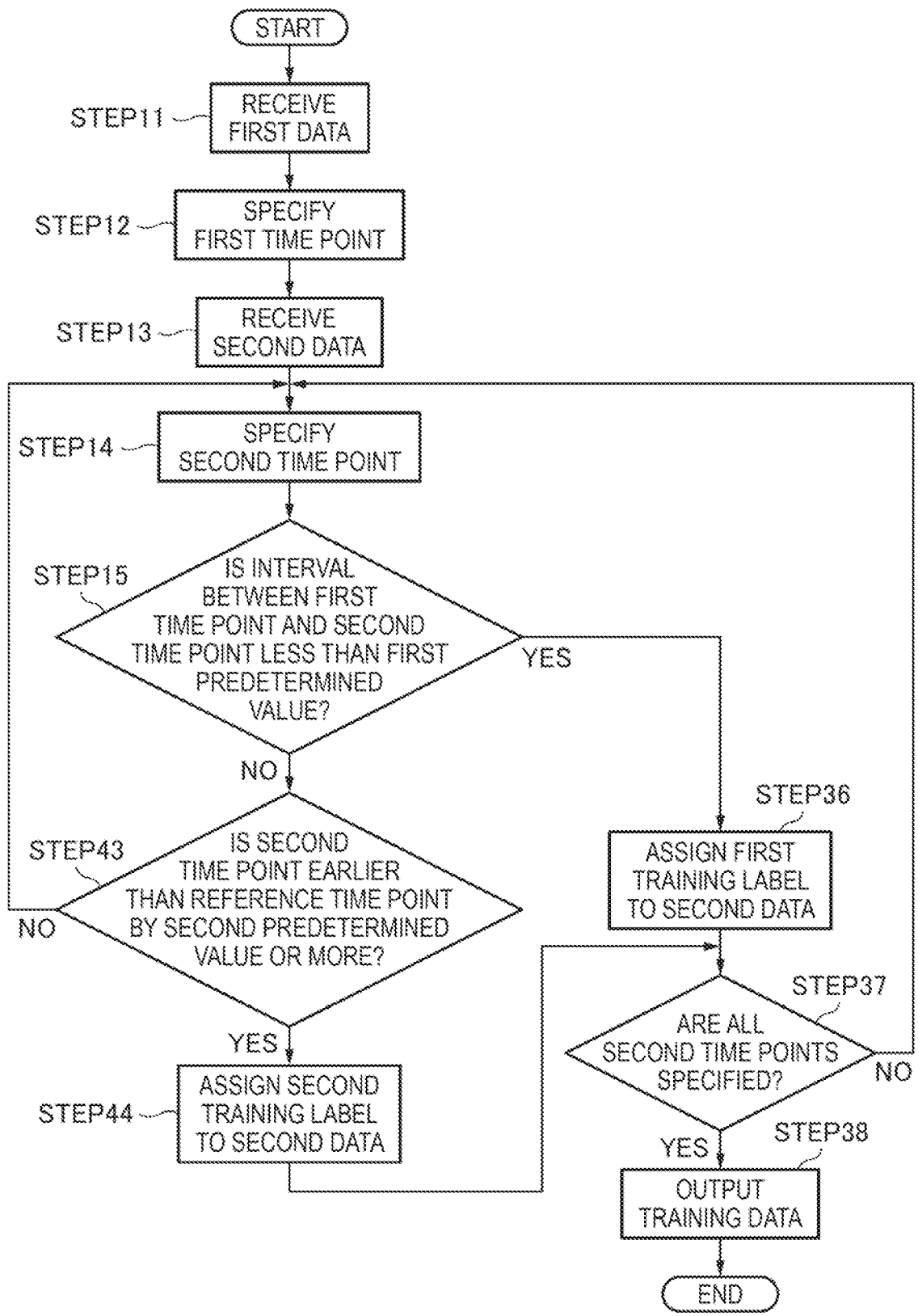
FIG. 11 illustrates another example of the flow of processing executed by the processing unit of FIG. 3.

FIG. 11 illustrates another example of the flow of processing that can be executed by the processing unit 62 of the training data generation device 60. Substantially the same processing elements as those described with reference to FIG. 5 are denoted by the same reference signs, and a repeated description thereof will be omitted.

When it is determined that the time interval between the second time point specified in STEP 14 and the first time point specified in STEP 12 is smaller than the first predetermined value T1 (YES in STEP 15), the processing unit 62 assigns a first training label indicating that atrial fibrillation has occurred, to the second data D2 subjected to the specification of the second time point in STEP 14 (STEP 36). At this time, a weighting index is not necessarily assigned.

Subsequently, the processing unit 62 determines whether the second time point is specified for all pieces of the second data D2 (STEP 37). When it is determined that the second time point is not specified for all pieces of the second data D2 (NO in STEP 37), the processing is returned to STEP 14, and the second time point is specified for another piece of second data D2.

When it is determined that the time interval is not smaller than the first predetermined value T1 (NO in STEP 15), the processing unit 62 determines whether the specified second time point is earlier than the reference time point t0 by the second predetermined value T2 or more (STEP 43). Examples of the reference time point t0 include a time point at which the present processing is performed, a time point at which the latest electrocardiogram waveform is obtained from the subject 31, a time point at which an electrocardiogram waveform, in which it is determined that atrial fibrillation has occurred, is obtained from the subject 31, and the like. The second predetermined value T2 may be the same as or different from the first predetermined value T1.

When it is determined that the specified second time point is earlier than the reference time point t0 by the second predetermined value T2 or more (YES in STEP 43), the processing unit 62 signs a second training label indicating that atrial fibrillation has not occurred, to the second data D2 obtained in STEP 13 (STEP 44).

Thereafter, the processing unit 62 determines whether the second time point is specified for all pieces of the second data D2 (STEP 37). When it is determined that the second time point is not specified for all pieces of the second data D2 (NO in STEP 37), the processing is returned to STEP 14, and the second time point is specified for another piece of second data D2.

When it is determined that the specified second time point is not earlier than the reference time point to by the second predetermined value T2 or more (NO in STEP 43), the processing is also returned to STEP 14, and the second time point is specified for another piece of second data D2.

In the example illustrated in FIG. 6, since the time point t1 and the time point t2 are earlier than the reference time point t0 by the second predetermined value T2 or more, the processing unit 62 assigns a second training label indicating that atrial fibrillation has not occurred, to the second data D2 that is based on the electrocardiogram waveforms obtained at the time point t1 and the time point t2, respectively.

Thereafter, the processing unit 62 outputs, from the output unit 63, the training data TR that includes both the second data D2, to which the first training label is assigned, and the second data D2 to which the second training label is assigned (STEP 38 of FIG. 11).

According to the processing according to the present example, based on electrocardiogram waveforms indicating sinus rhythm obtained from the same subject, it is possible to generate both training data, to which a training label indicating that atrial fibrillation has occurred is assigned, and training data for which it is determined that atrial fibrillation has not occurred. Accordingly, it is possible to enhance the effect of machine learning for classifying, based on presence or absence of the risk of occurrence of atrial fibrillation, electrocardiogram waveforms indicating sinus rhythm.

The training data TR generated by the training data generation device 60 described above can be used not only at the time of initial learning for generating the learned model 13 but also at the time of relearning of the learned model 13. This relearning is performed by the model generation device 50 in the same or similar manner as the initial learning. The relearning of the learned model 13 is performed at an appropriate timing. Examples of the appropriate timing include a time when a predetermined period elapses since the previous learning, a time when a predetermined number of pieces of training data TR are accumulated, and the like.

Each of the processing unit 62 of the training data generation device 60, the processing unit 52 of the model generation device 50, and the processing unit 12 of the prediction device 10 having the above-described functions may be implemented by a general-purpose microprocessor that operates in cooperation with a general-purpose memory. Examples of the general-purpose microprocessor include a CPU, an MPU, and a GPU. Examples of the general-purpose memory include a ROM and a RAM. In this case, a ROM may store a computer program that executes the above-described processing. The ROM is an example of a non-transitory computer-readable medium storing a computer program. The general-purpose microprocessor specifies at least a part of the program stored in the ROM, loads the program into a RAM, and executes the above-described processing in cooperation with the RAM. The computer program may be pre-installed in the general-purpose memory, or may be downloaded from an external server via a communication network and installed in the general-purpose memory. In this case, the external server is an example of a non-transitory computer-readable medium storing a computer program.

Each of the processing unit 62 of the training data generation device 60, the processing unit 52 of the model generation device 50, and the processing unit 12 of the prediction device 10 having the above-described functions may be implemented by a dedicated integrated circuit capable of executing the above-described computer program, such as a microcontroller, an ASIC, or an FPGA. In this case, the above computer program is pre-installed in a storage element provided in the dedicated integrated circuit. The storage element is an example of a computer-readable medium storing a computer program. Each of the processing unit 62 of the training data generation device 60, the processing unit 52 of the model generation device 50, and the processing unit 12 of the prediction device 10 having the above-described functions may be implemented by a combination of a general-purpose microprocessor and a dedicated integrated circuit.

Figure 12:
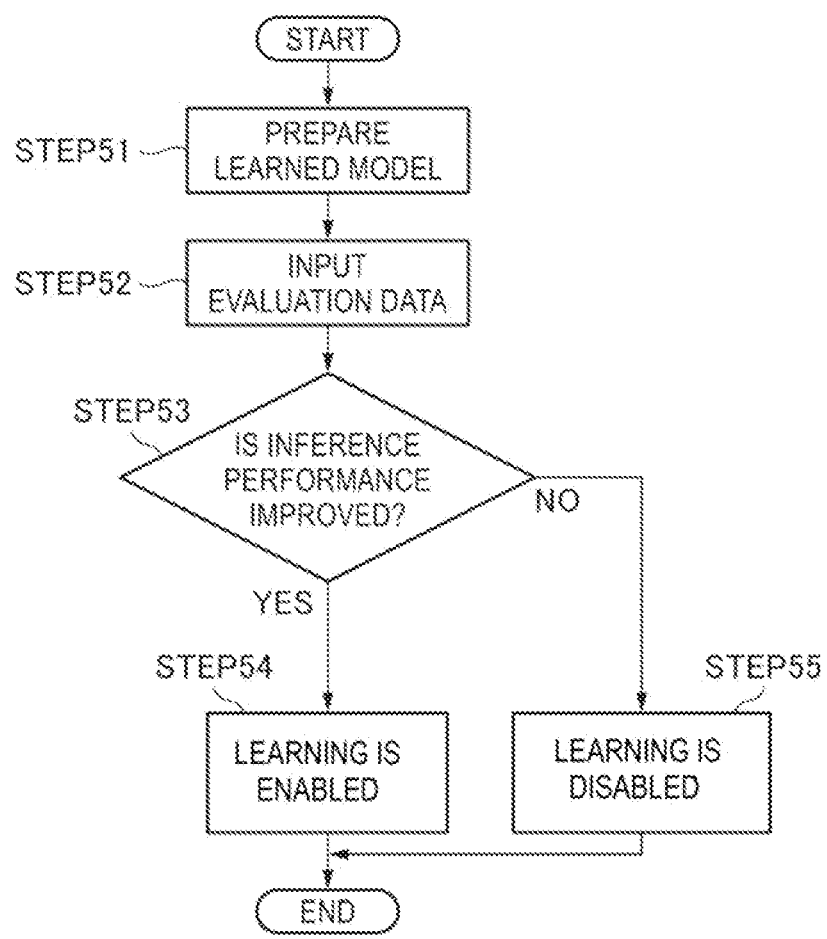
FIG. 12 illustrates a flow of processing executed by a model evaluation device of FIG. 2.

As illustrated in FIG. 2, the learned model 13 generated by the model generation device 50 can be used for evaluation to be performed by a model evaluation device 70 using evaluation data EV. FIG. 12 illustrates a flow of evaluation processing executed by the model evaluation device 70.

First, the learned model 13 is prepared (STEP 51). The learned model 13 may be a model that is subjected to initial learning or may be a model that is subjected to relearning.

Subsequently, the model evaluation device 70 inputs the evaluation data EV to the learned model 13 (STEP 52). The evaluation data EV includes, as information, an electrocardiogram waveform and an observation as to whether atrial fibrillation has occurred that is assigned to the electrocardiogram waveform. The evaluation data EV is selected so as to be different from any of the first data D1, the second data D2, and the third data D3 described above. The electrocardiogram waveform included in the evaluation data EV may be actually obtained from a subject, or may be obtained through a medical information database or the like.

Subsequently, based on an output of the learned model 13 with respect to the input evaluation data EV, the model evaluation device 70 determines whether prediction performance of the learned model 13 is improved (STEP 53). Specifically, it is determined whether an accuracy rate of a prediction result of predicting whether atrial fibrillation has occurred is proved, which is output from the learned model 13 with respect to the input of the same evaluation data EV for which whether atrial fibrillation has occurred is known.

When it is determined that the prediction performance of the learned model 13 is improved (YES in STEP 53), the latest machine learning that the learned model 13 is subjected to is enabled (STEP 54). When the learned model prepared in STEP 51 is subjected to initial learning, the prediction performance is improved in principle, and thus initial learning is defined. When the learned model prepared in STEP 51 is subjected to relearning, whether the prediction performance is improved is determined based on an output with respect to the re-input of the same evaluation data EV.

When it is determined that the prediction performance of the learned model 13 is not improved (NO in STEP 53), the latest machine learning the learned model 13 is subjected to is disabled (STEP 55).

According to such a configuration, it is possible to prevent an occurrence of a situation in which risk prediction performance of the prediction device 10 in which the learned model 13 is installed decreases due to over-learning or the like.

The processing executed by the model evaluation device 70 may be implemented by a general-purpose microprocessor that operates in cooperation with a general-purpose memory. Examples of the general-purpose microprocessor include a CPU, an MPU, and a GPU. Examples of the general-purpose memory include a ROM and a RAM. In this case, a ROM may store a computer program that executes the above-described processing. The ROM is an example of a non-transitory computer-readable medium storing a computer program. The general-purpose microprocessor specifies at least a part of the program stored in the ROM, loads the program into a RAM, and executes the above-described processing in cooperation with the RAM. The computer program may be pre-installed in the general-purpose memory, or may be downloaded from an external server via a communication network and installed in the general-purpose memory. In this case, the external server is an example of a non-transitory computer-readable medium storing a computer program.

The processing executed by the model evaluation device 70 may be implemented by a dedicated integrated circuit capable of executing the computer program, such as a microcontroller, an ASIC, or an FPGA. In this case, the above computer program is pre-installed in a storage element provided in the dedicated integrated circuit. The storage element is an example of a computer-readable medium storing a computer program. The processing executed by the model evaluation device 70 may be implemented by a combination of a general-purpose microprocessor and a dedicated integrated circuit.

The above embodiment is merely an example for facilitating understanding of the presently disclosed subject matter. The configurations according to the above embodiment can be appropriately changed or improved without departing from the gist of the presently disclosed subject matter.

In the above embodiment, the determination of whether the time interval between the first time point and the second time point is smaller than the first predetermined value T1 (STEP 15 in FIG. 5) is made for both before and after the first time point, as illustrated in FIG. 6. Alternatively, it may be determined whether the time interval from the second time point is smaller than the first predetermined value T1 for only one of before and after the first time point.

In the processing described with reference to FIG. 5, it is not necessary to always output, as the training data TR, both the second data D2 to which the first training label is assigned together with the weighting index and the third data D3 to which the second training label is assigned. The processing unit 62 of the training data generation device 60 may output only one of the second data D2 and the third data D3 from the output unit 63 as the training data TR as necessary.

In the processing described with reference to FIG. 11, it is not necessary to always output, as the training data TR, both the second data D2 to which the first training label is assigned and the second data D2 to which the second training label is assigned. The processing unit 62 of the training data generation device 60 may output only one of the second data D2 to which the first training label is assigned and the second data D2 to which the second training label is assigned, as the training data TR from the output unit 63 as necessary.

In the above embodiment, the model generation device 50 generates the learned model 13 through machine learning using a neural network. Alternatively, the learned model 13 may be generated through another machine learning algorithm. Examples of other machine learning algorithms include a decision tree, a random forest, a support vector machine, and the like.

In the above embodiment, the prediction device 10 is provided as a device independent of the electrocardiograph 20. The prediction device 10 may be disposed at a location where the prediction device 10 can be connected to the electrocardiograph 20 via wired communication or short-range wireless communication, or may be disposed at a location where the prediction device 10 can communicate with the electrocardiograph 20 via a local area network or a wide area network. Communication via a local area network or a wide area network may be wired or wireless.

Alternatively, the prediction device 10 may be built in the electrocardiograph 20. In this case, the output device 40 illustrated in FIG. 1 may be a part of the electrocardiograph 20 or may be a device independent of the electrocardiograph 20. Alternatively, the prediction device 10 may be built in another measurement device capable of obtaining an electrocardiogram. Examples of such a device include a physiological information monitor, a defibrillator, and the like.

When the training data generation device 60 and the model generation device 50 are provided as devices independent of each other, the output unit 63 of the training data generation device 60 and the reception unit 51 of the model generation device 50 may be connected so as to allow wired communication or wireless communication. That is, the output unit 63 and the reception unit 51 may be physical communication interfaces.

The training data generation device 60 and the model generation device 50 may be functional entities implemented in the same device. In this case, at least a part of the functions of the processing unit 62 of the training data generation device 60 may be implemented by the processing unit 52 of the model generation device 50. The output unit 63 and the reception unit 51 may be logical interfaces.

In the above embodiment, the risk of occurrence of atrial fibrillation in the subject 30 is predicted by the prediction device 10. However, a risk of development of another cardiac disease may be a target of prediction. Examples of other cardiac diseases include premature atrial contraction, paroxysmal supraventricular tachycardia, premature ventricular contraction, ventricular tachycardia, ventricular fibrillation, myocardial infarction, and the like. In accordance with a cardiac disease to be predicted, an appropriate electrocardiogram waveform that characterizes the cardiac disease is used in generating the training data TR.

A risk of development of a disease other than a cardiac disease may be a prediction target. Examples of other diseases include epilepsy seizure, hypotension, hypertension, apnea syndrome, and the like. When a risk of occurrence of epilepsy seizure is set as a prediction target, the training data TR may be generated based on a brain wave waveform obtained from the subject. When a risk of development of hypertension or hypotension is set as a prediction target, the training data TR may be generated based on a blood pressure waveform obtained from the subject. The blood pressure waveform corresponds to change over time in blood pressure of the subject that is invasively measured. When a risk of development of apnea syndrome is set as a prediction target, the training data TR may be generated based on a respiratory waveform obtained from the subject. The respiratory waveform corresponds to change over time in carbon dioxide concentration or the like accompanying respiration of the subject. Each of the brain wave waveform, the blood pressure waveform, and the respiratory waveform is an example of physiological information. In any case, an appropriate measurement device is used instead of the electrocardiograph.

The physiological information used in generating the training data TR is not necessarily a physiological signal waveform. The training data TR may be generated based on a physiological parameter value obtained from a subject. Examples of the physiological parameter value include a systolic peak time and a diastolic time in the blood pressure, a cardiac output, an expiration time in respiration, an inspiration time in respiration, a respiration time, and the like.

The aforementioned embodiments are summarized as follows.

A first aspect of the presently disclosed subject matter relates to a learned model generation method for generating a learned model for predicting a disease development risk of a subject based on physiological information obtained from the subject. The learned model generation method includes:
  receiving first data including the physiological information obtained from a first subject and a first result that a disease is developing, the first result being determined based on the physiological information;
  specifying a first time point at which the physiological information included in the first data is obtained;
  receiving second data including the physiological information obtained from the first subject and a second result that the disease is not developing, the second result being determined based on the physiological information;
  specifying a second time point at which the physiological information included in the second data is obtained;
  upon determining that a time interval between the first time point and the second time point is smaller than a first predetermined value, assigning, to the second data, a first training label indicating that the disease is developing and a weighting index that is capable of taking a plurality of values according to the time interval; and
  performing machine learning of a model by using the second data, to which the first training label is assigned, as training data.

A second aspect of the presently disclosed subject matter relates to A training data generation device that generates training data to be used in generating a learned model for predicting a disease development risk of a subject based on physiological information obtained from the subject. The training data generation device includes circuitry configured to:
- receive first data including the physiological information obtained from a first subject and a first result that a disease is developing, the first result being determined based on the physiological information;
- receive second data including the physiological information obtained from the first subject and a second result that the disease is not developing, the second result being determined based on the physiological information;
- specify a first time point at which the physiological information included in the first data is obtained;
- specify a second time point at which the physiological information included in the second data is obtained; and
- upon determining that a time interval between the first time point and the second time point is smaller than a first predetermined value, generate training data by assigning, to the second data, a first training label indicating that the disease is developing and a weighting index that is capable of taking a plurality of values according to the time interval.

Even for physiological information based on which it is determined that a disease is not developing, if a time interval between a time point at which the physiological information is obtained and a time point at which physiological information, based on which it is determined that the disease is developing, is obtained is not so long, there is a possibility that some factor that is a sign of the disease or some factor affected by the disease is included in physiological information determined not to be involved in the development of the disease. According to the configuration as described above, it is possible to generate training data, to which a training label indicating that a disease is developing is assigned, with respect to physiological information based on which it is determined that a disease satisfying such a temporal condition is not developing.

Therefore, a learned model, which is generated through machine learning using such training data, can output a prediction result that there is a risk of disease development, with respect to an input of physiological information based on which it can be determined that a disease is not developing. Accordingly, a disease development risk potentially possessed by a subject can be predicted.

In addition, a weighting index that can take a plurality of values according to the time interval is assigned to the first training label indicating that a disease is developing. Accordingly, it is possible to generate training data having a different probability of prediction of the disease development risk that is predicted based on the physiological information based on which it is determined that the disease is not developing. Therefore, it is possible to perform more precise machine learning, and thus it is possible to predict the disease development risk more precisely.

In the present embodiments, determining that a disease is developing also means determining that the disease has developed. Determining that a disease is not developing also means determining that the disease has not developed.

A third aspect of the presently disclosed subject matter relates to a learned model generation method for generating a learned model for predicting a disease development risk of a subject based on physiological information obtained from the subject. The learned model generation method includes:
- receiving first data including the physiological information obtained from a first subject and a first result that a disease is developing, the first result being determined based on the physiological information;
- specifying a first time point at which the physiological information included in the first data is obtained;
- receiving second data including the physiological information obtained from the first subject and a second result that the disease is not developing, the second result being determined based on the physiological information;
- specifying a second time point at which the physiological information included in the second data is obtained;
- assigning, to the second data, a first training label indicating that the disease is developing, upon determining that a time interval between the first time point and the second time point is smaller than a first predetermined value;
- assigning, to the second data, a second training label indicating that the disease is not developing, upon determining that the second time point is earlier than a reference time point by a second predetermined value or more; and
- performing machine learning of a model by using, as training data, at least one of the second data to which the first training label is assigned and the second data to which the second training label is assigned.

A fourth aspect of the presently disclosed subject matter relates to a training data generation device that generates training data to be used in generating a learned model for predicting a disease development risk of a subject based on physiological information obtained from the subject. The device includes circuitry configured to:
- receive first data including the physiological information obtained from a first subject and a first result that a disease is developing, the first result being determined based on the physiological information;
- receive second data including the physiological information obtained from the first subject and a second result that the disease is not developing, the second result being determined based on the physiological information; and
- specify a first time point at which the physiological information included in the first data is obtained;
- specify a second time point at which the physiological information included in the second data is obtained; and
- generate training data by assigning a first training label indicating that the disease is developing to the second data upon determining that a time interval between the first time point and the second time point is less than a first predetermined value, and by assigning a second training label indicating that the disease is not developing to the second data upon determining that the second time point is earlier than a reference time point by a second predetermined value or more.

When physiological information, based on which it is determined that a disease is not developing, is obtained sufficiently before a reference time point, there is a high probability that the physiological information does not include a factor involved in the development of the disease. According to each of the configurations according to the third and fourth aspects, the second training label indicating that the disease is not developing is actively assign to such physiological information and included in the training data. Accordingly, based on physiological information that is obtained from the same subject and based on which it is determined that the disease is not developing, it is possible to generate both the training data to which the training label indicating that the disease is developing is assigned and the training data for which it is determined that the disease is not developing. Therefore, it is possible to enhance the effect of machine learning for classifying the physiological information, based on which it is determined that the disease is not developing, based on presence or absence of a disease development risk.

The invention claimed is:

1. A learned model generation method for generating a learned model for predicting a disease development risk of a subject based on physiological information obtained from the subject, the learned model generation method comprising:
receiving first data including the physiological information obtained from a first subject and a first result that a disease is developing, the first result being determined based on the physiological information;
specifying a first time point at which the physiological information included in the first data is obtained;
receiving second data including the physiological information obtained from the first subject and a second result that the disease is not developing, the second result being determined based on the physiological information;
specifying a second time point at which the physiological information included in the second data is obtained;
upon determining that a time interval between the first time point and the second time point is smaller than a first predetermined value, assigning, to the second data, a first training label indicating that the disease is developing and a weighting index that is capable of taking a plurality of values according to the time interval; and
performing machine learning of a model by using the second data, to which the first training label is assigned, as training data.

2. The learned model generation method according to claim 1,
wherein the value of the weighting index decreases linearly, nonlinearly, or stepwise as the time interval from the first time point increases.

3. The learned model generation method according to claim 1, further comprising:
receiving third data including the physiological information obtained from a second subject different from the first subject and a third result that the disease is not developing, the third result being determined based on the physiological information;
specifying a third time point at which the physiological information included in the third data is obtained;
assigning, to the third data, a second training label indicating that the disease is not developing, when the third time point is earlier than a reference time point by a second predetermined value or more; and
performing machine learning of the model by using the third data, to which the second training label is assigned, as training data.

4. A learned model generation method for generating a learned model for predicting a disease development risk of a subject based on physiological information obtained from the subject, the learned model generation method comprising:
receiving first data including the physiological information obtained from a first subject and a first result that a disease is developing, the first result being determined based on the physiological information;
specifying a first time point at which the physiological information included in the first data is obtained;
receiving second data including the physiological information obtained from the first subject and a second result that the disease is not developing, the second result being determined based on the physiological information;
specifying a second time point at which the physiological information included in the second data is obtained;
assigning, to the second data, a first training label indicating that the disease is developing, upon determining that a time interval between the first time point and the second time point is smaller than a first predetermined value;
assigning, to the second data, a second training label indicating that the disease is not developing, upon determining that the second time point is earlier than a reference time point by a second predetermined value or more; and
performing machine learning of a model by using, as training data, at least one of the second data to which the first training label is assigned and the second data to which the second training label is assigned.

5. The learned model generation method according to claim 1,
wherein evaluation data is inputted to the model, the evaluation data including the physiological information and a third result indicating whether the disease is developing, the third result being determined based on the physiological information,
wherein whether prediction performance of the model is improved as compared with prediction performance before performing the machine learning is determined, and
wherein upon determining that the prediction performance is improved, the machine learning is enabled.

6. The learned model generation method according to claim 1, wherein the physiological information is a physiological signal waveform.

7. The learned model generation method according to claim 1, wherein the disease is a cardiac disease.

8. A training data generation device that generates training data to be used in generating a learned model for predicting a disease development risk of a subject based on physiological information obtained from the subject, the training data generation device comprising circuitry configured to:
receive first data including the physiological information obtained from a first subject and a first result that a disease is developing, the first result being determined based on the physiological information;
receive second data including the physiological information obtained from the first subject and a second result that the disease is not developing, the second result being determined based on the physiological information;
specify a first time point at which the physiological information included in the first data is obtained;
specify a second time point at which the physiological information included in the second data is obtained; and
upon determining that a time interval between the first time point and the second time point is smaller than a first predetermined value, generate training data by assigning, to the second data, a first training label indicating that the disease is developing and a weighting index that is capable of taking a plurality of values according to the time interval.

9. A training data generation device that generates training data to be used in generating a learned model for predicting a disease development risk of a subject based on physiological information obtained from the subject, the device comprising circuitry configured to:
- receive first data including the physiological information obtained from a first subject and a first result that a disease is developing, the first result being determined based on the physiological information;
- receive second data including the physiological information obtained from the first subject and a second result that the disease is not developing, the second result being determined based on the physiological information; and
- specify a first time point at which the physiological information included in the first data is obtained;
- specify a second time point at which the physiological information included in the second data is obtained; and
- generate training data by assigning a first training label indicating that the disease is developing to the second data upon determining that a time interval between the first time point and the second time point is less than a first predetermined value, and by assigning a second training label indicating that the disease is not developing to the second data upon determining that the second time point is earlier than a reference time point by a second predetermined value or more.

10. A learned model generation device that generates a learned model for predicting a disease development risk of a subject based on physiological information obtained from the subject, the device comprising circuitry configured to:
- receive training data generated by the training data generation device according to claim 8; and
- perform machine learning of a model by using the training data.

11. A disease development risk prediction device comprising circuitry configured to:
- receive physiological information obtained from a subject;
- input the physiological information to the learned model generated by the learned model generation device according to claim 10;
- predict a disease development risk of the subject based on a prediction result output from the learned model; and
- output information corresponding to the disease development risk.

12. A learned model generation device that generates a learned model for predicting a disease development risk of a subject based on physiological information obtained from the subject, the device comprising circuitry configured to:
- receive training data generated by the training data generation device according to claim 9; and
- perform machine learning of a model by using the training data.

13. A disease development risk prediction device comprising circuitry configured to:
- receive physiological information obtained from a subject;
- input the physiological information to the learned model generated by the learned model generation device according to claim 12;
- predict a disease development risk of the subject based on a prediction result output from the learned model; and
- output information corresponding to the disease development risk.

14. The learned model generation method according to claim 1, wherein the weighting index representing a degree to which teaching of the first training label is considered.

15. The training data generation device according to claim 8, wherein the weighting index representing a degree to which teaching of the first training label is considered.

16. The learned model generation method according to claim 4, wherein the physiological information is a physiological signal waveform.

* * * * *